United States Patent
Hatano

(10) Patent No.: US 9,931,024 B2
(45) Date of Patent: Apr. 3, 2018

(54) ENDOSCOPE

(71) Applicant: OLYMPUS CORPORATION, Tokyo (JP)

(72) Inventor: Keisuke Hatano, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/353,909

(22) Filed: Nov. 17, 2016

(65) Prior Publication Data
US 2017/0065151 A1 Mar. 9, 2017

Related U.S. Application Data

(63) Continuation of application No. PCT/JP2015/064715, filed on May 22, 2015.

(30) Foreign Application Priority Data

Sep. 16, 2014 (JP) .................. 2014-188041

(51) Int. Cl.
*A61B 1/005* (2006.01)
*A61B 1/00* (2006.01)
*A61B 1/05* (2006.01)

(52) U.S. Cl.
CPC ........ *A61B 1/0051* (2013.01); *A61B 1/00066* (2013.01); *A61B 1/00071* (2013.01); *A61B 1/00112* (2013.01)

(58) Field of Classification Search
CPC .............. A61B 1/0051; A61B 1/00112; A61B 1/00071; A61B 1/00066; A61B 1/00105; A61B 1/0014; A61B 1/0052
See application file for complete search history.

(56) References Cited

U.S. PATENT DOCUMENTS 5,377,668 A * 1/1995 Ehmsen ............. A61B 1/00165
600/121
2002/0133077 A1 9/2002 Edwardsen et al.
(Continued)

FOREIGN PATENT DOCUMENTS

EP 1832222 A2 9/2007
JP H07-000345 A 1/1995
(Continued)

OTHER PUBLICATIONS

International Search Report dated Aug. 18, 2015 issued in PCT/JP2015/064715.
(Continued)

*Primary Examiner* — Timothy J Neal
(74) *Attorney, Agent, or Firm* — Scully, Scott, Muphy & Presser, P.C.

(57) ABSTRACT

An endoscope includes: an operation portion; an insertion portion pivotable relative to the operation portion; a pivot state switching instruction portion; a sliding member slidable in a longitudinal axis direction of the operation portion along with a switching operation of the pivot state switching instruction portion; a holding ring configured to hold the sliding member; and a pivot restriction switching device provided with a braking member on an end portion on pivot portion side of the sliding member, and configured to switch over a state of a pivot portion from a pivotable state to a pivot restricted state or from the pivot restricted state to the pivotable state, the braking member being pressed against and disposed on the pivot portion to apply braking force.

5 Claims, 6 Drawing Sheets

(56) References Cited

U.S. PATENT DOCUMENTS

2007/0030344 A1* 2/2007 Miyamoto ......... A61B 1/00045
348/65
2007/0212913 A1 9/2007 Takeuchi et al.
2007/0225556 A1* 9/2007 Ortiz ................. A61B 1/00052
600/109
2007/0249904 A1* 10/2007 Amano ............. A61B 1/00052
600/131

FOREIGN PATENT DOCUMENTS

| | | | |
|---|---|---|---|
| JP | 2002-315750 | A | 10/2002 |
| JP | 2007-236543 | A | 9/2007 |
| JP | 2010-069108 | A | 4/2010 |
| JP | 2010-234058 | A | 10/2010 |

OTHER PUBLICATIONS

Japanese Office Action dated May 10, 2016 issued in JP 2016-501264.

* cited by examiner

ENDOSCOPE

CROSS REFERENCE TO RELATED APPLICATION

This application is a continuation application of PCT/JP2015/064715 filed on May 22, 2015 and claims benefit of Japanese Application No. 2014-188041 filed in Japan on Sep. 16, 2014, the entire contents of which are incorporated herein by this reference.

BACKGROUND OF THE INVENTION

1. Field of the Invention

The present invention relates to an endoscope in which an insertion portion is configured to be pivotable relative to an operation portion.

2. Description of the Related Art

An endoscope including an elongated flexible insertion portion is used in a medical field, an industrial field, and the like. The flexible insertion portion includes a distal end portion, a bending portion, and a flexible tube portion in order from distal end side. Further, an operation portion that is held and operated by an operator is provided at a proximal end portion of the insertion portion.

When the elongated insertion portion is inserted into a lumen including a plurality of branched parts such as bronchus, the operator typically inserts the elongated insertion portion to an objective site of a deep part by repeating an operation of bending the bending portion, an operation of twisting the operation portion and the insertion portion, and other operations.

Japanese Patent Application Laid-Open Publication No. 2010-69108 discloses an endoscope that makes it possible to prevent confusion between an operation of restricting pivot of an insertion portion and an operation of allowing the insertion portion to pivot relative to the operation portion, and makes it easy to perform the operation of allowing the insertion portion to pivot relative to the operation portion after restriction of the pivot of the insertion portion is cancelled. The endoscope includes, on an outer circumference of the insertion portion and the operation portion, a dial section that includes a pivot mechanism allowing the insertion portion to pivot relative to the operation portion and a pivot restriction mechanism restricting the pivot of the insertion portion relative to the operation portion.

SUMMARY OF THE INVENTION

An endoscope according to an aspect of the present invention includes: an operation portion that includes a longitudinal axis and is held by an operator; an insertion portion that is coupled to a distal end side of the operation portion through a pivot portion and is pivotable relative to the operation portion; a pivot state switching instruction portion that is operated by a finger of a hand of the operator holding the operation portion; a sliding member that is disposed at a position deviated from an insertion portion pivot axis in a radial direction and is slidable in the longitudinal axis direction of the operation portion along with a switching operation of the pivot state switching instruction portion; a holding ring that is provided on an inner peripheral surface of an operation portion side fixing pipe sleeve and holds the sliding member; and a pivot restriction switching device that includes the pivot state switching instruction portion and the sliding member, is provided with a braking member on an end portion on pivot portion side of the sliding member, and switches over a state of the pivot portion from a pivotable state to a pivot restricted state or from the pivot restricted state to the pivotable state, the braking member being pressed against and disposed on the pivot portion to apply braking force.

DETAILED DESCRIPTION OF THE PREFERRED EMBODIMENT(S)

Figure 1:
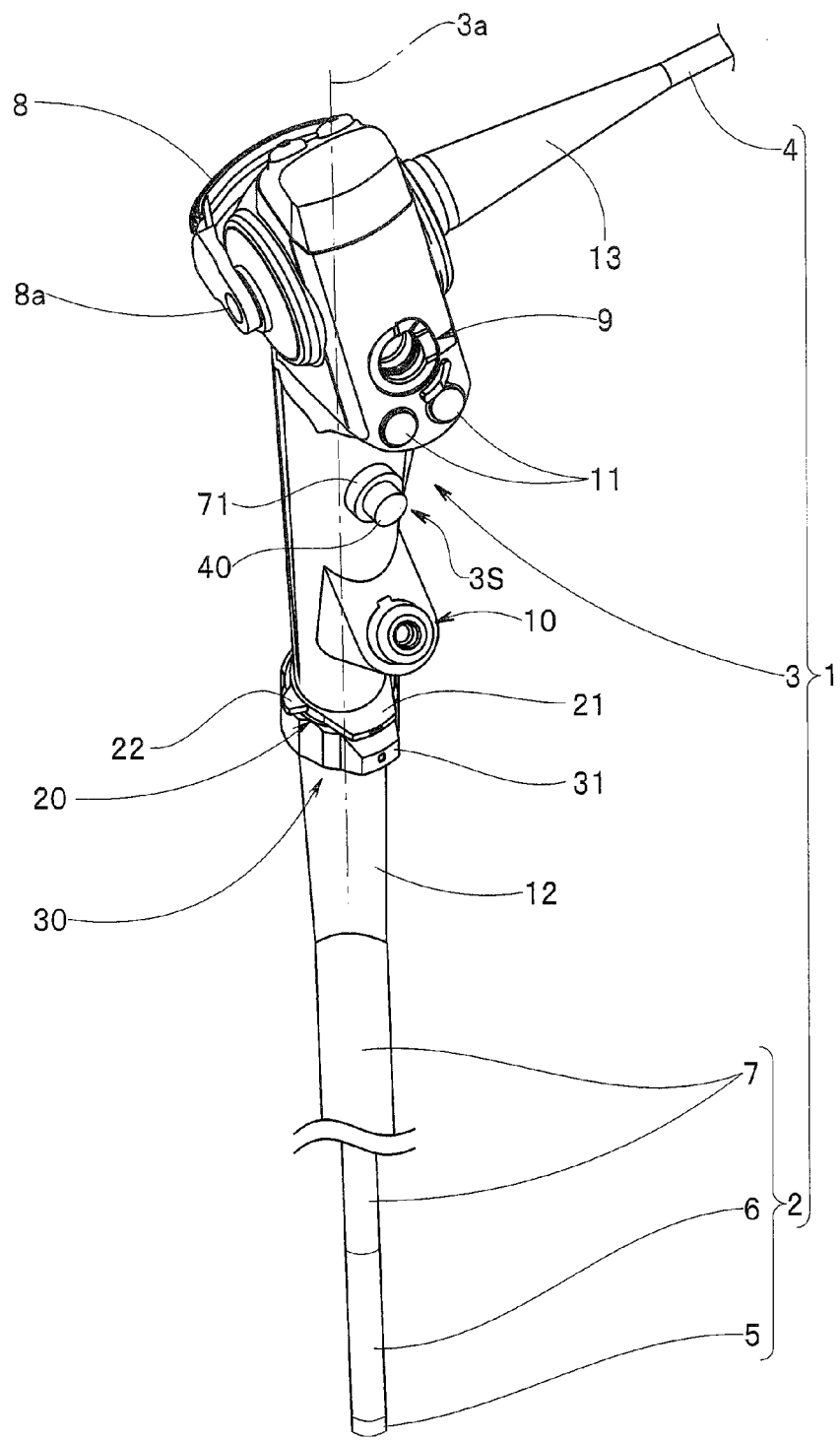
FIG. 1 is a diagram to explain a configuration of an endoscope.

An embodiment of the present invention is described below with reference to drawings.

Note that the respective drawings used for the following description provide schematic illustration. To illustrate respective components on the drawings to a recognizable extent, dimensional relationship, scales, and the like of respective members are illustrated with different scales for each component. The present invention is not limited to the number of components, the shapes of the respective components, the size ratio of the components, and relative positional relationship of the respective components that are illustrated in the drawings.

As illustrated in FIG. 1, an endoscope 1 includes an insertion portion 2, an operation portion 3, and a universal cord 4. The insertion portion 2 of the endoscope 1 according to the present embodiment is pivotable relative to the operation portion 3.

The insertion portion 2 includes a distal end rigid portion 5, a bending portion 6, and an elongated flexible tube 7 that are connected to one another in order from distal end side. The bending portion 6 is bendable in two directions.

The operation portion 3 is provided at a proximal end portion of the insertion portion 2. The operation portion 3 is provided with a bending lever 8, a suction cylinder 9, a treatment instrument insertion port 10, and various kinds of changeover switches 11. The operation portion 3 of the present embodiment is provided with a notification ring 20, a rotary knob 30, a pivot state switching instruction portion (hereinafter, referred to as an instruction switch) 40 of a pivot restriction switching device 3S, and the like.

In the present embodiment, the bending lever 8, the suction cylinder 9, the treatment instrument insertion port 10, the changeover switches 11, the instruction switch 40 that are provided on the operation portion 3 are laterally symmetrical about a reference line 3a of the operation portion 3. As a result, the bending lever 8, the suction cylinder 9, the changeover switches 11, and the instruction switch 40 are operable by fingers of a hand holding the operation portion 3, irrespective of a right hand or a left hand of the operator.

The changeover switches 11 are switches that generate a freeze signal, a release signal, or the like. Endoscope treatment instruments such as biopsy forceps not illustrated are inserted into the treatment instrument insertion port 10. A suction button not illustrated is arranged on the suction cylinder 9. The bending lever 8 is an operation device that bends the bending portion 6 in a vertical direction. The bending lever 8 is pivotally operable about a knob shaft 8a.

Note that a reference sign 12 indicates a first bend preventing member that covers the proximal end portion of the insertion portion 2 to prevent buckling of the insertion portion 2. A reference sign 13 indicates a second bend preventing member that covers a distal end portion of the universal cord 4 to prevent buckling of the universal cord 4.

Figure 2A:
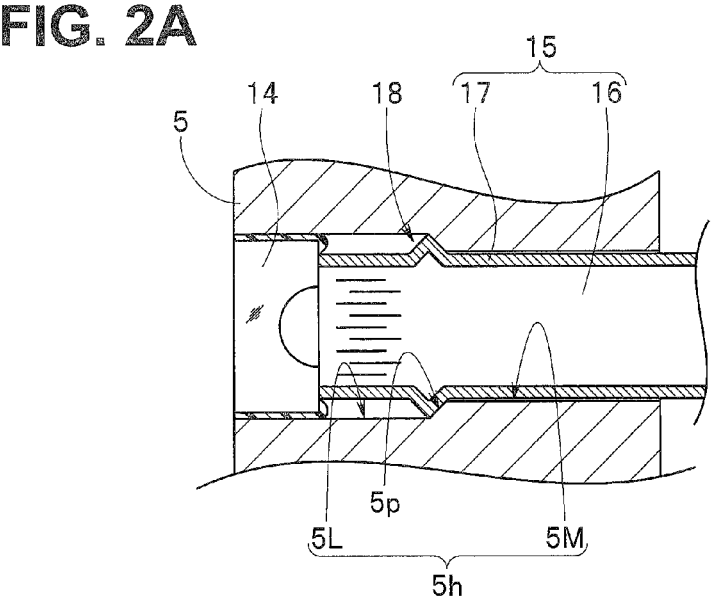
FIG. 2A is a diagram to explain an illumination optical system provided in a distal end rigid portion.

Also, in the present embodiment, an illumination lens 14 and a light guide unit 15 that configure an illumination optical system are provided in the distal end rigid portion 5, as illustrated in FIG. 2A. In the present embodiment, the light guide unit 15 is singularly exchangeable without being exchanged together with the distal end rigid portion 5.

More specifically, the light guide unit 15 includes a light guide bundle 16 and a front pipe sleeve 17. The light guide bundle 16 is formed to be elongated with a predetermined diameter size. The front pipe sleeve 17 is fixed to a predetermined position on distal end side of the light guide bundle 16.

In the distal end rigid portion 5, an illumination light through hole 5h in which the illumination lens 14 and the distal end portion of the light guide unit 15 are arranged is provided along a longitudinal center axis.

The illumination light through hole 5h includes a large-diameter hole 5L and a small-diameter hole 5M. The illumination lens 14 is bonded and fixed to the large-diameter hole 5L, and the front pipe sleeve 17 is disposed in the small-diameter hole 5M. A center axis of the large-diameter hole 5L is coincident with a center axis of the small-diameter hole 5M. A reference sign 5p indicates a positioning surface that is an inclined surface on which a proximal end side of an elastic convex portion 18 described later is disposed in a contact manner.

The front pipe sleeve 17 has a predetermined outer diameter that is smaller than an inner diameter of the small-diameter hole 5M. The elastic convex portion 18 that is elastically deformable is provided in a middle part of the front pipe sleeve 17. The elastic convex portion 18 has a predetermined outer diameter that is smaller than an inner diameter of the large-diameter hole 5L and is larger than the inner diameter of the small-diameter hole 5M.

Figure 2B:
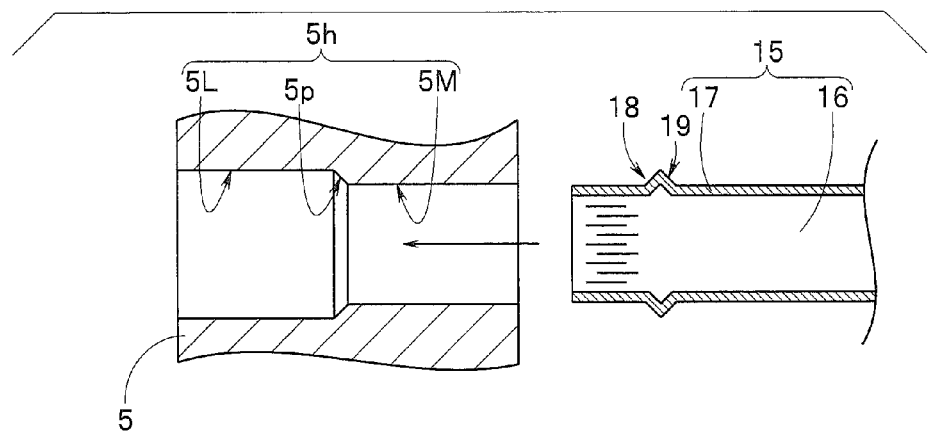
FIG. 2B is a diagram to explain the illumination optical system provided in the distal end rigid portion.
Figure 2C:
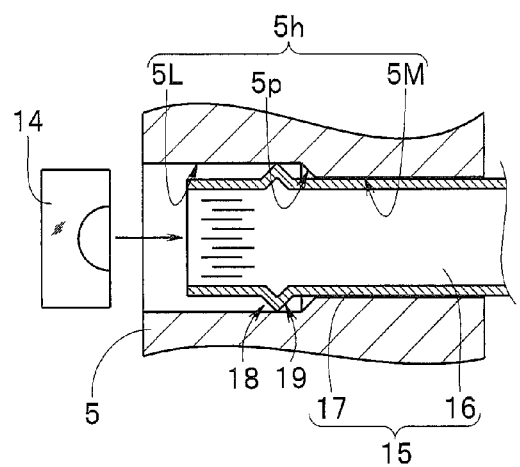
FIG. 2C is a diagram to explain the illumination optical system provided in the distal end rigid portion.

The front pipe sleeve 17 fixed to the light guide bundle 16 is inserted into the illumination light through hole 5h from a proximal end opening side as illustrated in FIG. 2B, and is placed inside the large-diameter hole 5L (refer to FIG. 2C). The elastic convex portion 18 is elastically deformed while the front pipe sleeve 17 passes through the small-diameter hole 5M, and is restored to an original shape after the front pipe sleeve 17 passes through the small-diameter hole 5M.

As illustrated in FIG. 2C, the illumination lens 14 is disposed inside the large-diameter hole 5L in a state in which the front pipe sleeve 17 fixed to the light guide bundle 16 is placed inside the large-diameter hole 5L. At this time, the illumination lens 14 is pushed into the large-diameter hole 5L such that a proximal end surface of the illumination lens 14 is brought into contact with a distal end surface of the front pipe sleeve 17 and a tapered surface 19 on the proximal end side of the elastic convex portion 18 is brought into contact with and disposed on the positioning surface 5p.

In the contact arrangement state, an adhesive is applied to a gap between the illumination lens 14 and the large-diameter hole 5L. Then, the illumination lens 14 is bonded and fixed to the distal end rigid portion 5 as illustrated in FIG. 2A, which results in completion of assembling.

As a result, the front pipe sleeve 17 and the light guide bundle 16 are disposed without being bonded and fixed to the illumination light through hole 5h of the distal end rigid portion 5.

The configuration makes it possible to exchange the light guide bundle 16 in the following manner when a failure occurs in the light guide bundle 16.

A worker disassembles the insertion portion 2 on the distal end rigid portion 5 side to expose the middle part of the light guide unit 15. The worker breaks down the illumination lens 14. The worker inserts a jig from the large-diameter hole 5L side to press an end surface of the jig against the distal end surface of the front pipe sleeve 17 of the light guide unit 15. The worker causes the elastic convex portion 18 to elastically deform while pushing the front pipe sleeve 17 with use of the jig, thereby gradually pushing out the front pipe sleeve 17 toward the proximal end side of the small-diameter hole 5M. Then, after removing the front pipe sleeve 17 from the small-diameter hole 5M, the worker detaches the light guide unit 15 from the distal end rigid portion 5. Thereafter, the worker assembles the light guide unit 15 and the illumination lens 14 in the illumination light through hole 5h in the above-described procedure illustrated in FIG. 2B and FIG. 2C, to complete the exchange.

Figure 3:
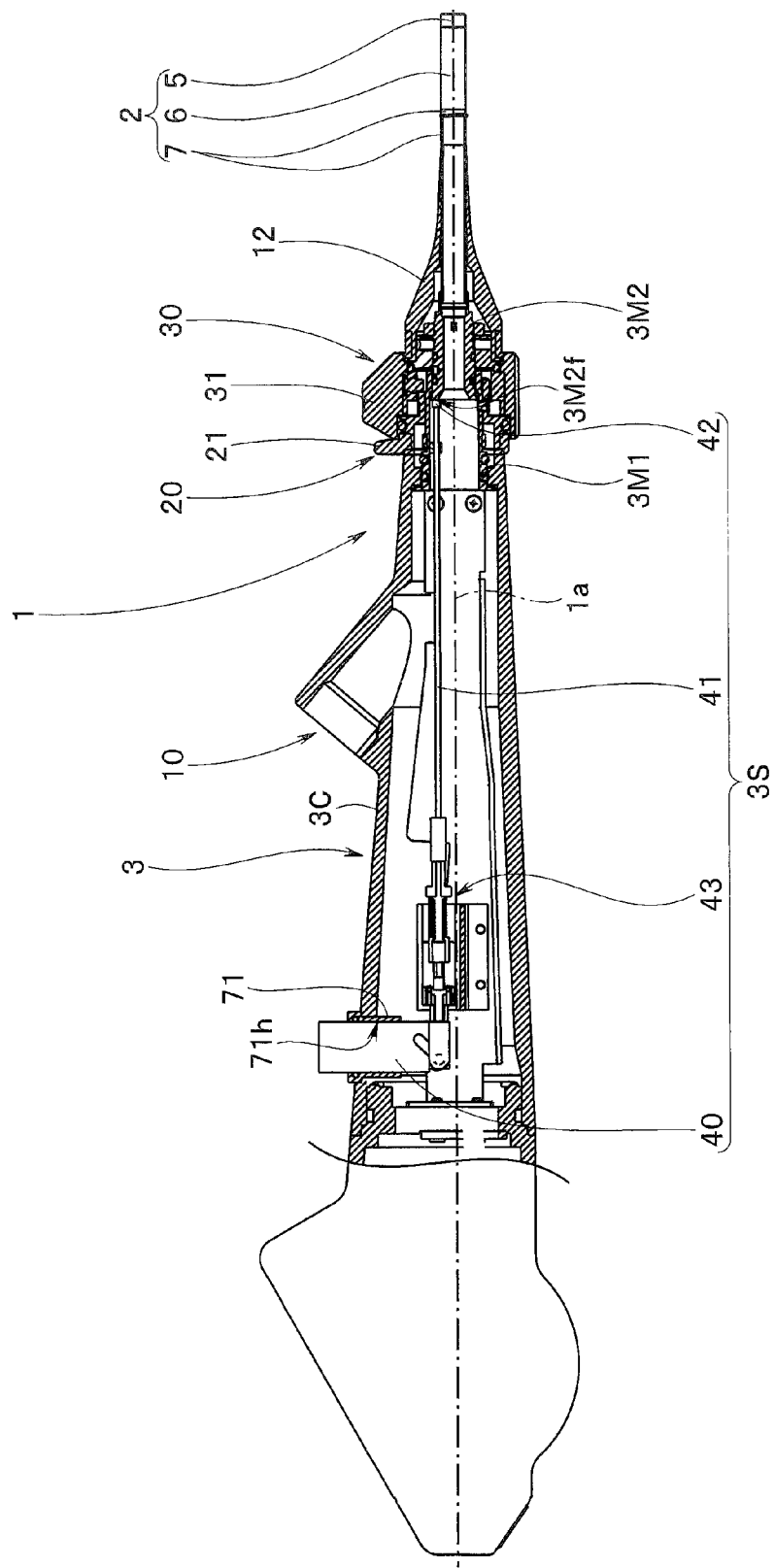
FIG. 3 is a diagram to explain a configuration inside an operation portion.

As illustrated in FIG. 3, a pivot connection mechanism and the pivot restriction switching device 3S are provided in the operation portion 3 of the present embodiment. The pivot connection mechanism rotatably connects the insertion portion 2 to the operation portion 3. The pivot restriction switching device 3S switches the state of the insertion portion 2 between a pivotable state relative to the operation portion 3 and a pivot restricted state.

The pivot connection mechanism that rotatably connects the insertion portion 2 to the operation portion 3 is described with reference to FIG. 3 and FIG. 4.

Figure 4:
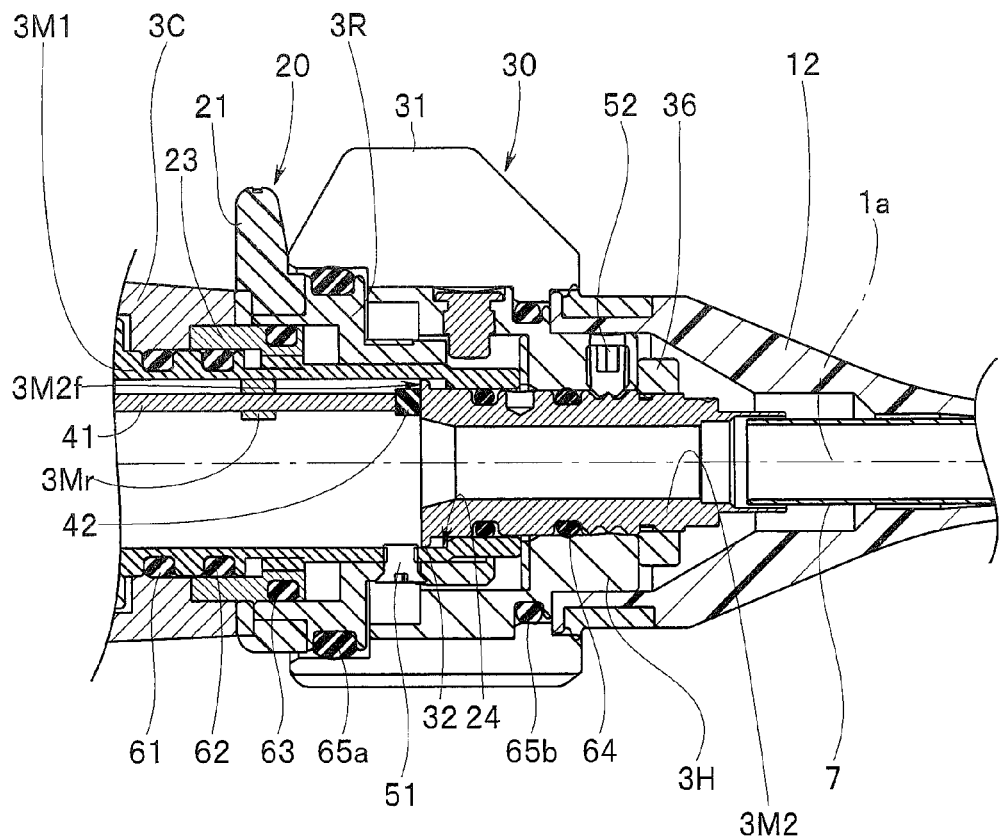
FIG. 4 is a diagram to explain a configuration of a connection part between an insertion portion and the operation portion.

As illustrated in FIG. 3 and FIG. 4, a cylindrical operation portion case body 3C, a pipe-shaped operation portion side fixing pipe sleeve 3M1, an annular notification ring fixing member 3R, a pipe-shaped pivot operation portion housing (hereinafter, abbreviated as a housing) 3H, and a pipe-shaped insertion portion side fixing pipe sleeve 3M2 are mainly provided at a connection part between the insertion portion 2 and the operation portion 3. The operation portion case body 3C is a main body of the operation portion. The insertion portion side fixing pipe sleeve 3M2 is a pivot portion.

The notification ring 20 is integrally attached to the notification ring fixing member 3R. The notification ring 20 is an annular member that includes an operation portion neutral position notification part 21 and, for example, a pair of pivot angle notification parts (refer to a reference sign 22 of FIG. 1) that are provided at respective predetermined positions and have respective predetermined outer shapes.

The operation portion side fixing pipe sleeve 3M1 is integrated with the operation portion case body 3C and the notification ring fixing member 3R.

The operation portion side fixing pipe sleeve 3M1 is provided with a male screw part (not illustrated), and a female screw part of a coupling member 23 is engaged with the male screw part. In the engaged state, the end of the distal end side of the operation portion side fixing pipe sleeve 3M1 projects from a distal end surface of the coupling member 23.

The end of the distal end side of the coupling member 23 is disposed inside the notification ring fixing member 3R. The notification ring fixing member 3R is integrally fastened and fixed to a predetermined position of the operation portion side fixing pipe sleeve 3M1 in the operation portion longitudinal axis direction by a first screw member 51.

The operation portion side fixing pipe sleeve 3M1 and a proximal end portion side of the coupling member 23 engaged with the fixing pipe sleeve 3M1 are disposed inside the operation portion case body 3C, and are integrally fixed to the operation portion case body 3C through engaging or bonding.

A reference sign 61 indicates a first O-shaped ring that secures watertightness between the operation portion case body 3C and the operation portion side fixing pipe sleeve 3M1. A reference sign 62 indicates a second O-shaped ring that secures watertightness between the operation portion side fixing pipe sleeve 3M1 and the coupling member 23. A reference sign 63 indicates a third O-shaped ring that secures watertightness between the coupling member 23 and the notification ring fixing member 3R.

In contrast, the insertion portion side fixing pipe sleeve 3M2 is integrated with the housing 3H and the insertion portion 2. The housing 3H is integrally attached with the rotary knob 30.

The rotary knob 30 is an annular member that includes an insertion portion neutral position notification part 31. The insertion portion neutral position notification part 31 is a convex part that projects from a predetermined outer peripheral surface of the rotary knob 30 and has a predetermined shape.

The housing 3H integrated with the rotary knob 30 is integrally fastened and fixed to a predetermined position of the insertion portion side fixing pipe sleeve 3M2 in the longitudinal axis direction by a second screw member 52. In addition, a proximal end portion of the flexible tube 7 configuring the insertion portion 2 is integrally fixed to the distal end side of the insertion portion side fixing pipe sleeve 3M2.

A reference sign 64 indicates a fourth O-shaped ring that secures watertightness between the housing 3H and the insertion portion side fixing pipe sleeve 3M2.

The insertion portion side fixing pipe sleeve 3M2 is a pivot portion that is pivotally disposed inside a through hole of the operation portion side fixing pipe sleeve 3M1. A center axis of the insertion portion side fixing pipe sleeve 3M2 and a center axis of the operation portion side fixing pipe sleeve 3M1 are coaxial with an insertion portion pivot axis 1a.

A flange 32 is provided at an end portion of the insertion portion side fixing pipe sleeve 3M2. A step 24 is provided on an inner peripheral surface of the end portion of the operation portion side fixing pipe sleeve 3M1. The flange 32 is caught on the step 24, which prevents the insertion portion side fixing pipe sleeve 3M2 from falling off from the operation portion side fixing pipe sleeve 3M1.

A reference sign 36 indicates a fixing adjuster ring. The fixing adjuster ring 36 is disposed to be engaged with a male screw part that is formed on an outer circumference of the insertion portion side fixing pipe sleeve 3M2. The fixing adjuster ring 36 sets contact between the flange 32 of the insertion portion side fixing pipe sleeve 3M2 and the step 24 of the operation portion side fixing pipe sleeve 3M1 to an appropriate state.

A reference sign 65a is an O-shaped ring that secures watertightness between the rotary knob 30 and the notification ring fixing member 3R. A reference sign 65b is an O-shaped ring that secures watertightness between the rotary knob 30 and the housing 3H.

In the present embodiment, the proximal end side of the flexible tube 7 of the insertion portion 2 and the first bend preventing member 12 are held and the pivot operation about the longitudinal axis is performed, or the rotary knob 30 is held and the pivot operation about the insertion portion pivot axis 1a is performed. This makes it possible to cause the insertion portion side fixing pipe sleeve 3M2 that is integrated with the housing 3H and the insertion portion 2, in the clockwise direction or the counterclockwise direction relative to the operation portion side fixing pipe sleeve 3M1 that is integrated with the operation portion case body 3C, the notification ring fixing member 3R, and the notification ring 20.

Note that a reference sign 41 indicates a sliding member having rigidity, for example, a shaft. A reference sign 42 is a braking member, for example, an elastic member such as a brake pad having predetermined elastic force. A reference sign 3Mr is a holding ring that is provided singularly or in plurality on the inner peripheral surface of the operation portion side fixing pipe sleeve 3M1 to hold the shaft 41.

The pivot restriction switching device is described with reference to FIG. 3, FIG. 5A, and FIG. 6.

When the instruction switch 40 provided on the operation portion 3 is pressed down, the state of the endoscope 1 of the present embodiment is switched to a state in which the brake pad 42 is pressed against and disposed on the proximal end surface 3M2f of the insertion portion side fixing pipe sleeve 3M2 to generate braking force and the pivot of the insertion portion 2 relative to the operation portion 3 is accordingly restricted by the braking force, or to a state in which the generation of the braking force is cancelled and the insertion portion 2 is pivotable relative to the operation portion 3.

More specifically, the pivot restriction switching device 3S is provided with the instruction switch 40, the shaft 41, the brake pad 42, and a switching section 43.

The instruction switch 40 is a cylindrical shaft body. The instruction switch 40 is disposed in a switch hole 71h of a fitting portion 71 that is provided in the operation portion case body 3C configuring the operation portion 3. The instruction switch 40 freely advances and retreats inside the switch hole 71h in a direction orthogonal to the insertion portion pivot axis 1a.

The fitting portion 71 is provided on the suction cylinder 9 side of the operation portion 3 between the suction cylinder 9 and the treatment instrument insertion port 10 so as to allow a holding hand to operate the instruction switch 40 without difficulty.

A cam groove 40c and a release groove 40g that are paired are provided at an end portion of the instruction switch 40 disposed inside the operation portion 3. A conversion member 44 described later is disposed in the release groove 40g.

Watertightness of a gap between the instruction switch 40 and the fitting portion 71 is secured by an O-shaped ring, and watertightness of a gap between the fitting portion 71 and the operation portion case body 3C is secured by, for example, an adhesive.

The switching section 43 is provided between the instruction switch 40 and the shaft 41.

The shaft 41 is a rod-like member. The brake pad 42 is provided on one of end portions of the shaft 41, and the coupling member 72 is provided on the other end portion. The shaft 41 is disposed in proximity to the inner peripheral surface of the through hole of the operation portion side fixing pipe sleeve 3M1 as illustrated in FIG. 4. In other words, the shaft 41 is deviated from the insertion portion pivot axis 1a by a predetermined distance in a radial direction, which avoids interference with the light guide bundle 16 and other components. The insertion portion pivot axis 1a is coaxial with the reference line 3a. The brake pad 42 is pressed against and disposed on the proximal end surface 3M2f of the insertion portion side fixing pipe sleeve 3M2 with predetermined pressure, thereby generating braking force.

In the state in which the insertion portion 2 is pivotable relative to the operation portion 3, the distal end surface of the brake pad 42 is so disposed as to be brought into contact with the proximal end surface 3M2f of the insertion portion side fixing pipe sleeve 3M2 or as to be separated by a distance shorter than a movable range of the shaft 41, in order to prevent the brake pad 42 from generating the braking force with respect to the proximal end surface 3M2f of the insertion portion side fixing pipe sleeve.

The switching section 43 includes the conversion member 44, a housing pipe 45, a knock rod 46, a rotor 47, a coil spring 48, and spring retainers 49a and 49b.

Note that the switching section 43 is a so-called knock type extending switch mechanism.

The conversion member 44 is formed in a substantially rectangular parallelepiped shape. A cam pin 44p is disposed upright on each of one side surface and a surface opposite to the one side surface. A pair of cam pins 44p are disposed in the cam groove 40c of the instruction switch 40.

Figure 5A:
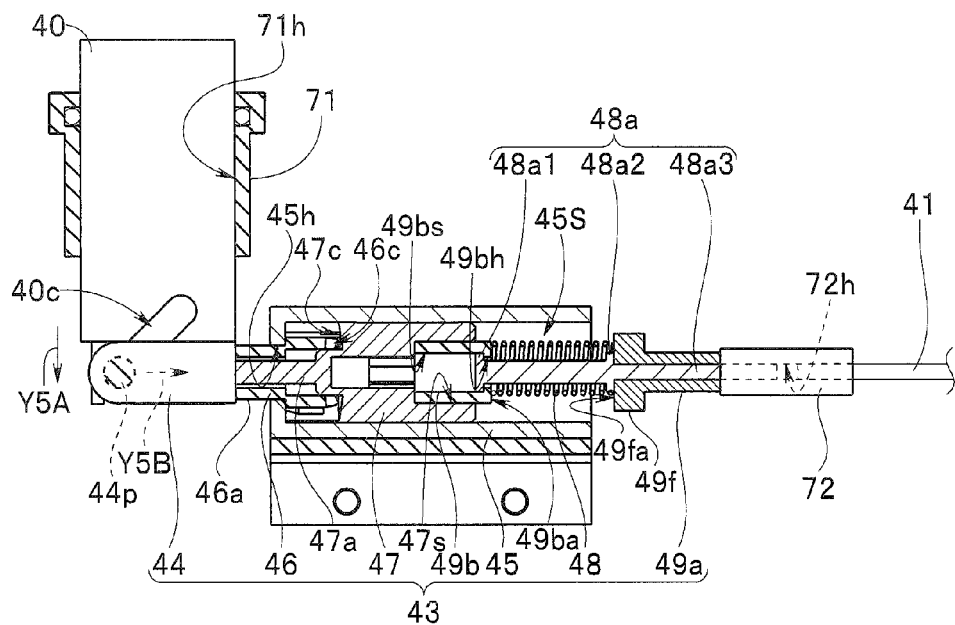
FIG. 5A is a diagram to explain a configuration of a pivot restriction switching device in a state in which the insertion portion is pivotable relative to the operation portion.
Figure 6:
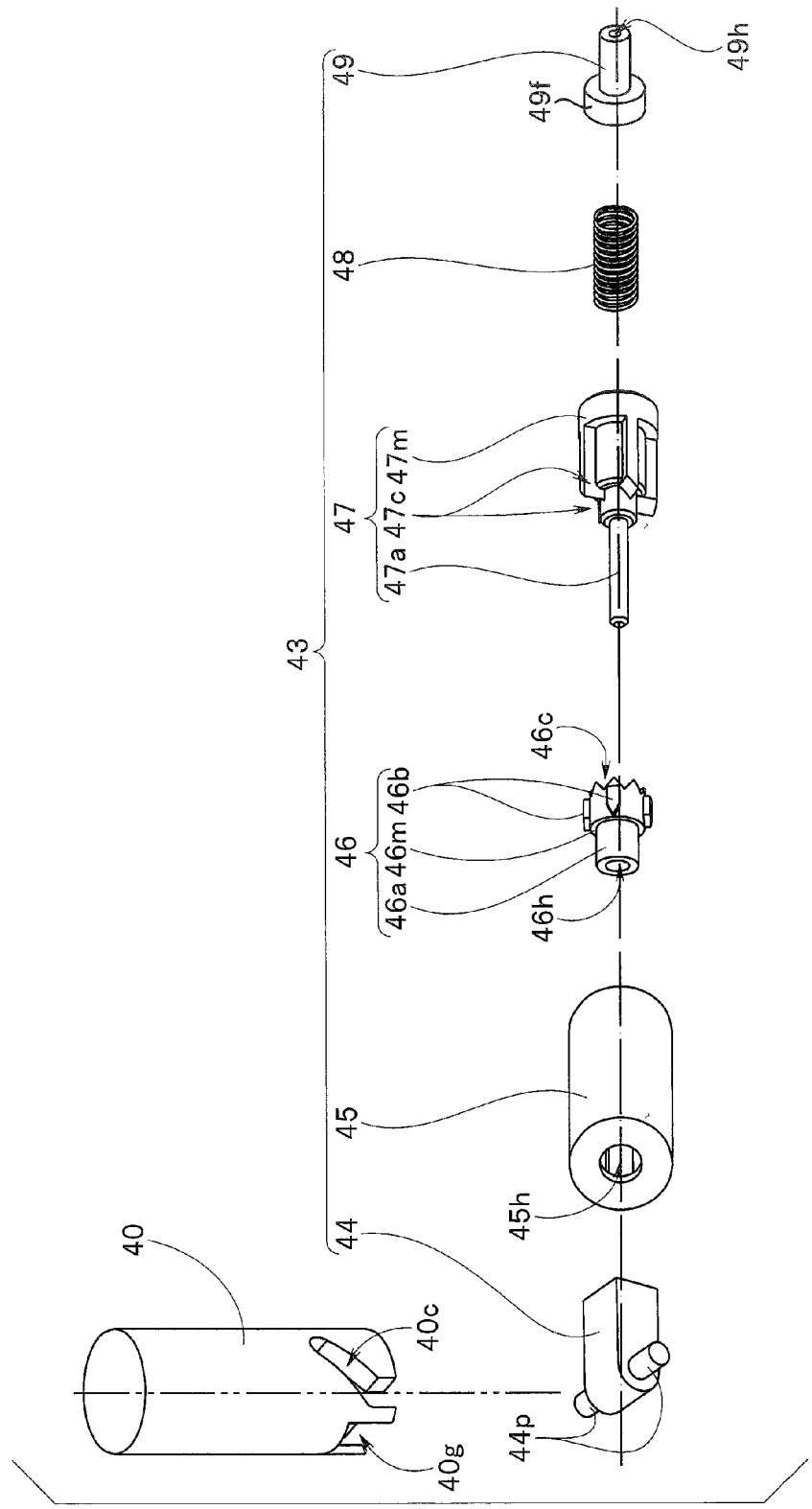
FIG. 6 is an exploded perspective view of the pivot restriction switching device.

In the present embodiment, causing the instruction switch 40 to move in an arrow Y5A direction in FIG. 5A that is orthogonal to the insertion portion pivot axis 1a causes the cam pins 44p to move along the cam groove 40c in an arrow Y5B direction in FIG. 5A along the insertion portion pivot axis 1a. This further causes the conversion member 44 to move toward the insertion portion along the axis 1a. The conversion member 44 is a sliding member advancing and retreating in the insertion portion pivot axis 1a direction.

The housing pipe 45 has a cylindrical shape and has an internal space 45S. In the internal space 45S, the knock rod 46, the rotor 47, and the coil spring 48 are disposed. A reference sign 45h indicates a through hole that extends in the axial direction to connect the internal space 45S with the outside.

In the through hole 45h, a knock shaft 46a of the knock rod 46 is so disposed as to project to the outside.

Further, an end surface of the knock shaft 46a projecting to the outside is oppositely disposed to be in contact with or in proximity to the end surface of the conversion member 44.

The knock rod 46 includes a rod main body 46m, the knock shaft 46a, and a protrusion part 46b. The knock shaft 46a is a round rod body projecting from one end surface side of the rod main body 46m. The protrusion part 46b projects from an outer peripheral surface of the rod main body 46m to the outside. A concave-convex part 46c is provided on the other surface side of the rod main body 46m that is opposite to the knock shaft 46a.

A reference sign 46h indicates a rotor insertion hole that is a through hole around the center axis of the knock rod 46.

The knock shaft 46a is slidably disposed inside the through hole 45h. In other words, the knock shaft 46a is so provided as to project from and retract into the housing pipe 45. The rod main body 46m having the protrusion part 46b of the knock rod 46 linearly moves inside the internal space 45S in the axial direction along with the projection and retraction of the knock shaft 46a.

The rotor 47 includes a rotor main body 47m, a projecting part 47a, and a cam 47c. The rotor main body 47m has an outer diameter substantially equivalent to the inner diameter of the internal space 45S. An outer peripheral surface of the rotor main body 47m is a sliding surface that smoothly rotates and slides inside the internal space 45S of the housing pipe 45.

The projecting part 47a is a round rod body projecting from one end surface side of the rotor main body 47m. The projecting part 47a is slidably and pivotally inserted and disposed inside the rotor insertion hole 46h of the knock rod 46. The cam 47c has a shape that is brought into contact with the concave-convex part 46c of the knock rod 46. The concave-convex part 46c moves along the cam 47c along with the projection and retraction of the knock rod 46. Accordingly, the rotor 47 slides while being rotated about the axis inside the internal space 45S.

The coil spring 48 is an elastic member that has predetermined biasing force. The coil spring 48 causes the instruction switch 40 to locate at a first position in a first compressed state illustrated in FIG. 5A. When the instruction switch 40 is moved to a second position illustrated in FIG. 5B, the coil spring 48 is put into a second compressed state to apply braking force to the brake pad 42.

The first spring retainer 49a has, on an end side of the first spring retainer, a flange 49f that projects from the outer peripheral surface to the outside. One end side of the coil spring 48 is disposed to contact with an end surface 49fa of the flange 49f. The other end side of the coil spring 48 is disposed on an end surface 49ba of the second spring retainer 49b. The second spring retainer 49b is a cylindrical member that has a concave part 49bs with a predetermined depth and a through hole 49bh.

A reference sign 48a indicates a shaft body. The shaft body 48a includes an end portion flange 48a1, a middle part flange 48a2, and a coupling shaft 48a3. A distance between the end portion flange 48a1 and the middle part flange 48a2 is set to a predetermined length, and defines a position at which the one end of the coil spring 48 is disposed. Further, a distance from the distal end surface of the brake pad 42 to the end surface 49fa of the flange 49f in the insertion portion pivot axis 1a direction is set to a predetermined length.

Note that the end portion flange 48a1 has an outer diameter smaller than an inner diameter of the concave part 49bs, and the middle part flange 48a2 has an outer diameter smaller than an inner diameter of the coil spring 48.

The coupling shaft 48a3 is inserted into a center through hole (denoted by a reference sign 72h in FIG. 5A) from an opening side formed in the coupling member 72, and is then integrally fixed to the coupling member 72 through, for example, bonding. The shaft 41 is inserted into the center through hole 72h from the other opening side of the coupling member 72, and is integrally fixed to the coupling member 72 through bonding similarly.

A reference sign 47s indicates a spring retainer disposing hole, and the second spring retainer 49b is integrally fixed to the rotor 47 through engaging, bonding, or the like.

An action of the pivot restriction switching device 3S is described.

The endoscope operator presses down the instruction switch 40 positioned at the first position illustrated in FIG. 5A, by a finger of a hand holding the operation portion 3. In response, the instruction switch 40 moves as mentioned above against the biasing force of the coil spring 48, which causes the conversion member 44 to gradually move toward the insertion portion along the insertion portion pivot axis 1a. Then, the end surface of the conversion member 44 is brought into contact with the end surface of the knock shaft 46a, and then the projection length of the knock shaft 46a is gradually decreased.

The knock rod 46 moves inside the internal space 45S along with the decrease of the projection length of the knock shaft 46a. As a result, a V-shaped distal end of the concave-convex part 46c is caught on the end portion of the cam 47c of the rotor 47 along with the movement of the knock rod 46, which causes the rotor 47 to slide and move and to rotate in a predetermined direction. Then, the protrusion part 46b of the knock rod 46 is caught on the cam 47c along with the rotation and movement of the rotor 47 to stops the moved rotor 47. At this time, the coil spring 48 has been put into the second compressed state. Also, the instruction switch 40 is stopped at the second position.

When the coil spring 48 is gradually shifted from the first compressed state to the second compressed state, the biasing force of the coil spring 48 is transmitted to the shaft 41. As a result, the pressing force of the distal end surface of the brake pad 42 pressing the proximal end surface 3M2f is gradually increased, and when the coil spring 48 is put to the second compressed state, the predetermined braking force acts from the brake pad 42 to the proximal end surface 3M2f, which results in the pivot restricted state.

Figure 5B:
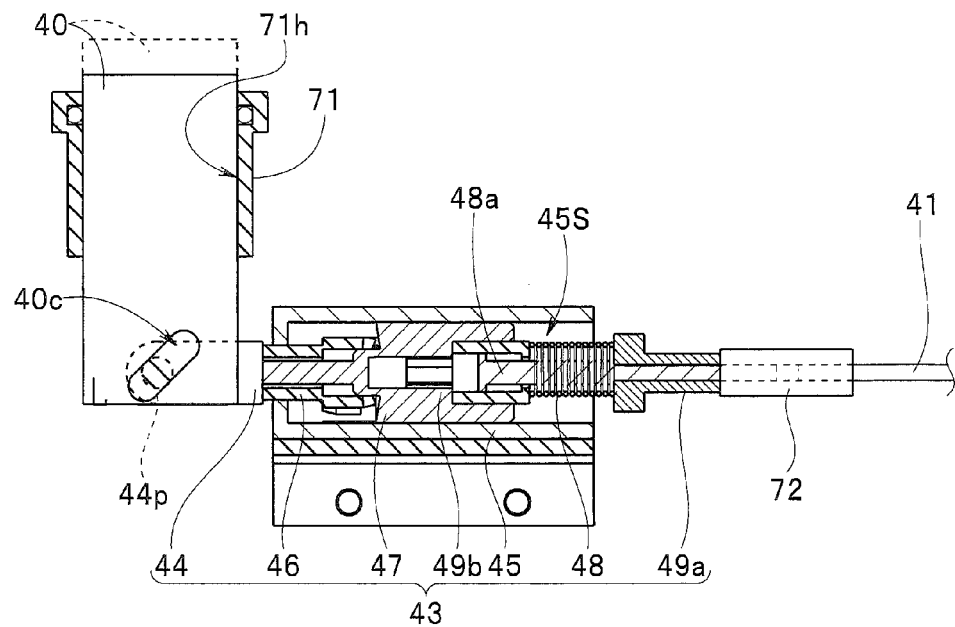
FIG. 5B is a diagram to explain the configuration of the pivot restriction switching device in a state in which pivot of the insertion portion relative to the operation portion is restricted.

Note that, in the pivot restricted state, to cancel the pivot restricted state and to put the state into the pivotable state, the operator presses down again the instruction switch 40 that is positioned at the second position illustrated in FIG. 5B. In response, the conversion member 44 further decreases the projection length of the knock shaft 46a. This causes the rotor 47 to further rotate in the predetermined direction along with the movement of the knock rod 46, and the protrusion part 46b is moved and released from the cam 47c. Then, the end surface of the concave-convex part 46c is separated away from the cam 47c by the biasing force of the coil spring 48.

In other words, the rotor 47 and the knock rod 46 are moved inside the internal space 45S in a direction opposite to the above-described direction by the biasing force of the coil spring 48, and the projection length of the knock shaft 46a is gradually increased. Further, the conversion member 44 is also gradually moved in the opposite direction along with the movement of the knock shaft 46a. The instruction switch 40 returns to the first position along with the movement of the conversion member 44.

At this time, the coil spring 48 returns from the second compressed state to the first compressed state, and the braking force is not applied from the distal end surface of the brake pad 42 to the proximal end surface 3M2f.

In this way, the knock type extending mechanism that is adopted to a knock type ballpoint pen is used as the pivot restriction switching mechanism of the switching section 43. Accordingly, the operator can press down the instruction switch 40 by a finger of the hand holding the operation portion 3 without releasing the hand from the insertion portion 2, to perform an operation of switching over the state from the pivotable state in which the insertion portion 2 is pivotable relative to the operation portion 3 to the pivot restricted state, or from the pivot restricted state to the pivotable state.

Note that, in the above-described embodiment, the brake pad 42 is used as the braking member. The braking member, however, is not limited to the above-described brake pad 42, and may be a brake pad having other shape. Also, the configuration of the braking member is not limited to the configuration in which the distal end surface of the braking member is pressed against the proximal end surface 3M2f to apply the braking force, and may be a configuration in which the braking force is applied, by the biasing force of the coil spring 48, to the inner peripheral surface of the insertion portion side fixing pipe sleeve 3M2, a configuration in which the braking force is applied by holding a braking member provided on the insertion portion side fixing pipe sleeve 3M2, or other configuration. Further, the elastic member is not limited to the coil spring 48, and may be an elastic tube body having predetermined biasing force, or the like.

In addition, in the above-described embodiment, the shaft 41 is used as the sliding member. The shaft 41 may preferably have a straight shape; however, the shaft 41 may be a shaft including a crank-shaped bending part in the middle part of the shaft. Moreover, the shaft 41 may be inserted into a coil shaft to define the position at which the sliding member is disposed.

The inventions of the embodiment as mentioned above are not limited to the embodiment and modifications, and various modifications may occur in embodiments without departing from the scope of the inventions.

According to the present invention, it is possible to realize an endoscope that allows an operator to perform an operation of switching over the pivot restricted state in which the pivot of the insertion portion relative to the operation portion is restricted, to the pivotable state, or the pivotable state to the pivot restricted state inversely, without causing the operator to release the hand from the insertion portion during the operation.

What is claimed is:

1. An endoscope, comprising:
an operation portion that includes a longitudinal axis and is configured to be held by an operator;
an insertion portion that is coupled to a distal end side of the operation portion through a pivot portion and is pivotable relative to the operation portion;
a pivot state switching instruction portion configured to be operated by a finger of a hand of the operator holding the operation portion;
a sliding member that is disposed at a position deviated from an insertion portion pivot axis in a radial direction and is slidable in the longitudinal axis direction of the operation portion along with a switching operation of the pivot state switching instruction portion;
a holding ring that is provided on an inner peripheral surface of an operation portion side fixing pipe sleeve and holds the sliding member; and
a pivot restriction device that includes the pivot state switching instruction portion and the sliding member, is provided with a braking member on an end portion on a pivot portion side of the sliding member, and switches over a state of the pivot portion from a pivotable state to a pivot restricted state or from the pivot restricted state to the pivotable state, the braking member being pressed against and disposed on the pivot portion to apply a braking force.

2. The endoscope according to claim 1, wherein
the sliding member comprises a rigid shaft, and
the braking member comprises a first elastic member configured to be pressed by the sliding member with application of the braking force to the sliding member.

3. The endoscope according to claim 2, wherein the pivot restriction switching device includes, at a position between the pivot state switching instruction portion and the sliding member, a second elastic member that applies the braking force to the sliding member.

4. The endoscope according to claim 3, wherein the pivot restriction switching device includes, at a position between the pivot state switching instruction portion and the sliding member, a knock type extending mechanism that switches over a state of the second elastic member from a first compressed state to a second compressed state or from the second compressed state to the first compressed state.

5. The endoscope according to claim 3, wherein the second elastic member is a coil spring.

* * * * *

UNITED STATES PATENT AND TRADEMARK OFFICE
CERTIFICATE OF CORRECTION

PATENT NO. : 9,931,024 B2
APPLICATION NO. : 15/353909
DATED : April 3, 2018
INVENTOR(S) : Keisuke Hatano Page 1 of 1

It is certified that error appears in the above-identified patent and that said Letters Patent is hereby corrected as shown below:

In the Claims

Column 10, Claim 1, Line 62:
a pivot restriction switching device that includes the pivot state Signed and Sealed this
Sixteenth Day of April, 2019

Andrei Iancu
*Director of the United States Patent and Trademark Office*